US009259436B2

(12) United States Patent
Chesson et al.

(10) Patent No.: US 9,259,436 B2
(45) Date of Patent: *Feb. 16, 2016

(54) POLY(UREA-URETHANE) COMPOSITIONS USEFUL AS TOPICAL MEDICAMENTS AND METHODS OF USING THE SAME

(71) Applicant: Chesson Laboratory Associates, Inc., Durham, NC (US)

(72) Inventors: Jerry S. Chesson, Durham, NC (US); Timothy J. Romack, Winterville, NC (US); Lance L. Swick, Durham, NC (US); David R. Terry, Wilton, CT (US)

(73) Assignee: Chesson Laboratory Associates, Inc., Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/229,341

(22) Filed: Mar. 28, 2014

(65) Prior Publication Data

US 2014/0212370 A1     Jul. 31, 2014

Related U.S. Application Data

(63) Continuation of application No. 12/244,272, filed on Oct. 2, 2008, now Pat. No. 8,771,725.

(60) Provisional application No. 60/979,573, filed on Oct. 12, 2007, provisional application No. 61/022,059, filed on Jan. 18, 2008.

(51) Int. Cl.
| | |
|---|---|
| *A61K 31/785* | (2006.01) |
| *A61L 26/00* | (2006.01) |
| *C08L 75/00* | (2006.01) |
| *A61K 8/87* | (2006.01) |
| *A61K 9/00* | (2006.01) |
| *A61K 47/08* | (2006.01) |
| *A61K 47/10* | (2006.01) |
| *A61K 47/18* | (2006.01) |
| *A61K 47/22* | (2006.01) |
| *A61K 47/26* | (2006.01) |
| *A61Q 19/00* | (2006.01) |
| *A61K 9/70* | (2006.01) |
| *A61K 45/06* | (2006.01) |

(52) U.S. Cl.
CPC .............. *A61K 31/785* (2013.01); *A61K 8/87* (2013.01); *A61K 9/0014* (2013.01); *A61K 9/7015* (2013.01); *A61K 45/06* (2013.01); *A61K 47/08* (2013.01); *A61K 47/10* (2013.01); *A61K 47/18* (2013.01); *A61K 47/22* (2013.01); *A61K 47/26* (2013.01); *A61L 26/0019* (2013.01); *A61L 26/0052* (2013.01); *A61Q 19/00* (2013.01); *A61K 9/7069* (2013.01); *C08L 75/00* (2013.01)

(58) Field of Classification Search
None
See application file for complete search history.

(56) References Cited

U.S. PATENT DOCUMENTS

| | | | |
|---|---|---|---|
| 3,438,374 A | 4/1969 | Falb at al. | |
| 3,551,364 A | 12/1970 | McGarr | |
| 3,893,969 A | 7/1975 | Wood | |
| 3,949,742 A | 4/1976 | Nowakowski | |
| 4,127,124 A | 11/1978 | Glagett et al. | |
| 4,328,322 A | 5/1982 | Baron | |
| 4,474,900 A | 10/1984 | Dominguez | |
| 4,542,012 A | 9/1985 | Dell | |
| 4,560,555 A * | 12/1985 | Snider | 514/772.1 |
| 4,581,432 A | 4/1986 | Blum et al. | |
| 4,584,192 A | 4/1986 | Dell et al. | |
| 4,652,493 A | 3/1987 | Reichmann et al. | |
| 4,655,210 A | 4/1987 | Edenbaum et al. | |
| 4,720,535 A | 1/1988 | Schleier et al. | |
| 4,733,659 A | 3/1988 | Edenbaum et al. | |
| 4,806,614 A | 2/1989 | Matsuda et al. | |
| 4,913,897 A | 4/1990 | Chvapil et al. | |
| 4,960,620 A | 10/1990 | House et al. | |
| 5,013,813 A | 5/1991 | Zimmerman et al. | |
| 5,039,775 A | 8/1991 | Oyaizu | |
| 5,091,497 A | 2/1992 | Grogler et al. | |
| 5,104,930 A | 4/1992 | Rinde et al. | |
| 5,160,328 A | 11/1992 | Cartmell et al. | |
| 5,192,536 A | 3/1993 | Huprich | |
| 5,319,058 A | 6/1994 | Hattori et al. | |
| 5,346,692 A | 9/1994 | Wohlrab et al. | |
| 5,374,704 A | 12/1994 | Muller et al. | |
| 5,445,597 A | 8/1995 | Clark et al. | |
| 5,616,677 A | 4/1997 | Primeaux, II et al. | |
| 5,738,627 A | 4/1998 | Kovacs et al. | |
| 5,763,734 A | 6/1998 | Nachtman et al. | |

(Continued)

FOREIGN PATENT DOCUMENTS

| | | |
|---|---|---|
| CA | 2 247 906 C | 9/1997 |
| EP | 0 230 387 A2 | 7/1987 |

(Continued)

OTHER PUBLICATIONS

Air Products and Chemicals, Inc.; Material Safety Data Sheet for Versalink* P-1000 Oligomeric Diamine.
Arch Chemicals, Inc.: Material Safety Data Sheet for POLY-A® 27-2000.
BASF Corporation; Material Safety Data Sheet for No. 218 Isocyanate.
BASF Corporation: Material Safety Data Sheet for Lupranate® 81 Isocyanate.
Bayer Corporation; Material Safety Data Sheet for Desmophen NH 1420.

(Continued)

*Primary Examiner* — H. Sarah Park
(74) *Attorney, Agent, or Firm* — Myers Bigel Sibley & Sajovec, P.A.

(57) ABSTRACT

The present invention provides a method of treating a skin ailment including administering to a subject in need thereof, a therapeutically effective amount of a composition including (i) a primary diamine; (ii) a secondary aromatic diamine; (iii) a polyisocyanate; and (iv) optionally, a polyol. The present invention also provides a method of forming a skin bandage.

22 Claims, 2 Drawing Sheets

(56) References Cited

U.S. PATENT DOCUMENTS

| | | | |
|---|---|---|---|
| 5,908,378 | A | 6/1999 | Kovacs et al. |
| 6,358,503 | B1 | 3/2002 | Gerrish |
| 6,359,100 | B1 | 3/2002 | Hostettler et al. |
| 6,403,063 | B1 | 6/2002 | Sawyer |
| 6,495,119 | B1 | 12/2002 | Sturla et al. |
| 6,552,155 | B1 | 4/2003 | Gutman et al. |
| 6,585,967 | B2 | 7/2003 | Narang et al. |
| 6,602,496 | B2 | 8/2003 | Hedgpeth et al. |
| 6,627,216 | B2 | 9/2003 | Brandt et al. |
| 6,746,667 | B2 | 6/2004 | Badejo et al. |
| 6,784,273 | B1 | 8/2004 | Spaans et al. |
| 6,833,408 | B2 | 12/2004 | Sehl et al. |
| 6,958,154 | B2 | 10/2005 | Brandt et al. |
| 7,078,475 | B2 | 7/2006 | Klein et al. |
| 2001/0051135 | A1 | 12/2001 | Sturla et al. |
| 2002/0037310 | A1 | 3/2002 | Jonn et al. |
| 2002/0147462 | A1 | 10/2002 | Mair et al. |
| 2003/0007826 | A1 | 1/2003 | Badejo et al. |
| 2003/0007946 | A1 | 1/2003 | Narang et al. |
| 2003/0007947 | A1 | 1/2003 | Narang |
| 2003/0007948 | A1 | 1/2003 | Hedgpeth |
| 2003/0007949 | A1 | 1/2003 | Hedgpeth et al. |
| 2003/0008011 | A1 | 1/2003 | Mershon |
| 2003/0080151 | A1 | 5/2003 | D'Alessio et al. |
| 2003/0180341 | A1 | 9/2003 | Gooch et al. |
| 2004/0137067 | A1 | 7/2004 | Narang et al. |
| 2004/0223932 | A1 | 11/2004 | Hedgpeth et al. |
| 2004/0241130 | A1 | 12/2004 | Tamareselvy et al. |
| 2004/0242770 | A1 | 12/2004 | Feldstein et al. |
| 2005/0033251 | A1 | 2/2005 | Toreki et al. |
| 2005/0073146 | A1 | 4/2005 | Daehne |
| 2005/0181977 | A1 | 8/2005 | Hunter et al. |
| 2005/0271794 | A1 | 12/2005 | DeSimone et al. |
| 2006/0173111 | A1 | 8/2006 | Karpowicz et al. |
| 2006/0216267 | A1* | 9/2006 | Kovacs et al. ............... 424/78.27 |
| 2007/0041935 | A1 | 2/2007 | Salamone et al. |
| 2007/0048355 | A1 | 3/2007 | Perlman |
| 2008/0253984 | A1 | 10/2008 | Kovacs et al. |

FOREIGN PATENT DOCUMENTS

| | | |
|---|---|---|
| EP | 0 409 550 B1 | 1/1991 |
| EP | 0 815 760 A2 | 1/1998 |
| EP | 0 572 416 B1 | 6/1998 |
| EP | 0 867 473 A1 | 8/1998 |
| EP | 0 625 914 B1 | 3/2005 |
| EP | 1 581 568 B1 | 7/2006 |
| JP | 2006-212426 | 8/2006 |
| WO | WO 86/05391 A1 | 9/1986 |
| WO | WO 95/19751 A1 | 7/1995 |
| WO | WO 98/02189 A2 | 1/1998 |
| WO | WO 02/22072 A2 | 3/2002 |
| WO | WO 2004/024779 A2 | 3/2004 |
| WO | WO 2004/032713 A2 | 4/2004 |
| WO | WO 2005/092276 A1 | 10/2005 |
| WO | WO 2006/101955 A2 | 9/2006 |
| WO | WO 2007/021620 A2 | 2/2007 |
| WO | WO 2007/021707 A2 | 2/2007 |
| WO | WO 2007/025293 A2 | 3/2007 |
| WO | WO 2007/062381 A2 | 5/2007 |

OTHER PUBLICATIONS

Bayer Corporation: Material Safety Data Sheet for Desmodur N 3200.

Dorf Ketal Chemicals, Inc.: Material Safety Data Sheet for Unilink 4200.

Dow Chemical Company: Material Safety Data Sheet for Isonate* 143L Modified MDI.

Elchueva et al., "Synthesis of Single-Component Urethane Sealants", Russian Journal of Applied Chemistry, vol. 74:5, pp. 860-863 (2001), Translated From Zharnal Prikladnoi Khimil, vol. 74:5, pp. 833-837 (2001).

House, et al., "The Versatility of UOPT™ and Clearlink™ Diamines in Polyurethane and Polyurea Systems", UTECH Asia 1996 Conference Paper, 16 pages.

Huntsman: Material Safety Data Sheet for JAD2000; Jeffamine® D-2000.

Huntsman: Material Safety Data Sheet for Rubinate® 9236.

Huntsman: Material Safety Data Sheet for Rubinate® 9259.

Lai et al., "A Cross Self-Curing System for an Aqueous-based PU Hybrid", Journal of Applied Polymer Science, vol. 97, pp. 550-558 (2005).

Reddinger et al., "Tuning the Properties of Polyurea Elastomer Systems via Raw Material Selection and Processing Parameter Modulation", PU Latin America 2001, Rapra Conference Proceedings, 2001, 9 pages.

Scott et al., "The Effect of Unilink 4200 on Spray Polyurea Coatings", UPO LLC, Hunstman Polyurea Training Seminar, Aug. 27, 2001, 24 pages.

Ubaghs et al., "Novel intramolecular blocked isocyanates as stable one-component systems for poly(urea urethane)s", Polymer, vol. 46, pp. 1459-1465 (2005).

Notification of Transmittal of the International Search Report and the Written Opinion of the International Searching Authority, or the Declaration corresponding to International Application No. PCT/US2008/011561 mailed Aug. 7, 2009.

Chinese Office Action dated Jun. 29, 2011 corresponding to Chinese Patent Application No. 200880121151.5, corresponding to PCT/US2008/011561 (English Translation).

Examination Report corresponding to Indian Patent Application No. 2497/DELNP/2010 (2 pages) (dated Apr. 23, 2015).

* cited by examiner

POLY(UREA-URETHANE) COMPOSITIONS USEFUL AS TOPICAL MEDICAMENTS AND METHODS OF USING THE SAME

CROSS REFERENCE TO RELATED APPLICATION

This application is a continuation of U.S. application Ser. No. 12/244,272, filed on Oct. 2, 2008, now allowed, which claims priority from U.S. Provisional Application Ser. Nos. 60/979,573 filed Oct. 12, 2007 and 61/022,059 filed Jan. 18, 2008, the disclosures of which are hereby incorporated by reference herein in their entireties.

FIELD OF THE INVENTION

The present invention relates to topical medicaments for treating skin ailments. The present invention also relates to the topical medicaments for treating bacterial, viral and fungal infections. The present invention also relates to methods of treating skin ailments, to methods of forming poly(urea-urethane) skin bandages, and to methods of treating bacterial, viral and fungal infections.

BACKGROUND OF THE INVENTION

Skin is the largest organ of the human body and is responsible for a number of bodily functions, including protection, temperature regulation, absorption and excretion necessary for bodily regulation, etc. Skin aliments or disorders, however, may retard the skin's function and may limit its ability to protect the body. Moreover, skin ailments may cause irritation, discomfort and/or pain to an inflicted individual.

Examples of skin ailments include rashes, including those caused by contact with rash-causing source, such as poison sumac, poison oak, poison ivy; bites or stings, such as from bees, yellow jackets, wasps, spiders, mosquitoes, cats and dogs; burns, such as first or second degree burns; sunburn; rosacea; sores, such as bed sores and Herpes sores; Kaposi's sarcoma and other skin ailments associate with HIV and/or AIDS; scarring, such as from surgery or via keloid scarring; warts, such as plantar warts; hemorrhoids; anal sphincter muscle tears; and cuts and scrapes, and the like.

There remains a need in the art for compositions that are effective in treating these and other ailments, ameliorating their symptoms, such as pain, discomfort and/or swelling, and reducing or preventing infection. Furthermore, it would be desirable for such compositions to be available as "one pot" or "single component" formulations. It would also be desirable for such compositions to be useful for more than one of these skin ailments, so as to be a multi-purpose medicament for various skin ailments.

There also remains a need in the art for compositions that can be used to treat viral, bacterial and fungal infections of the skin. Such skin infections may result from other skin ailments, or the skin infections may occur independently of any other skin ailment. Environments such as hospitals and nursing and retirement homes may have a relatively high risk for developing and transmitting antibiotic resistant bacteria. Compositions that can be used to treat antibiotic resistant bacteria would therefore be particularly desirable for use in these environments.

SUMMARY OF THE INVENTION

The present invention provides a method of treating a skin ailment comprising administering to a subject in need thereof, a therapeutically effective amount of a composition comprising (i) a primary polyamine; (ii) a polyisocyanate; and (iii) optionally, a polyol. The present invention also provides a method of forming a skin bandage comprising providing a composition comprising (i) a primary polyamine, (ii) a polyisocyanate, and (iii) optionally, a polyol, to a portion of skin of a subject; and allowing the composition to cure on the skin of the subject.

DETAILED DESCRIPTION OF EMBODIMENTS OF THE INVENTION

Figure 1:
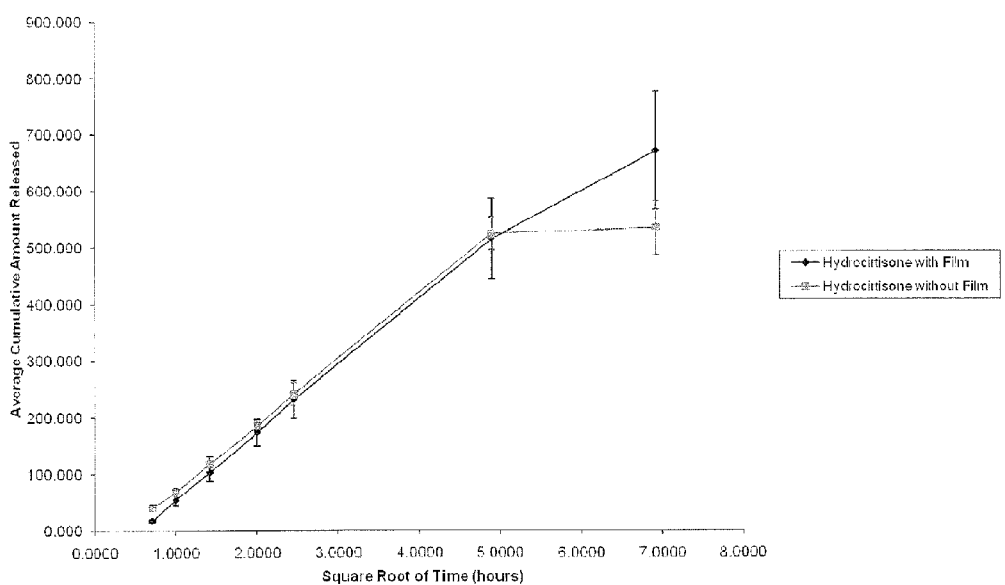
FIG. 1 is a graph illustrating the release of formulchon comprising Example 1 and a hydrocortisone medicament through a nylon membrane.

The invention is described more fully hereinafter. This invention may, however, be embodied in many different forms and should not be construed as limited to the embodiments set forth herein. Rather, these embodiments are provided so that this disclosure will be thorough and complete, and will fully convey the scope of the invention to those skilled in the art.

The terminology used herein is for the purpose of describing particular embodiments only and is not intended to be limiting of the invention. As used herein, the term "and/or" includes any and all combinations of one or more of the associated listed items. As used herein, the singular forms "a", "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein. All patents, patent applications and publications referred to herein are incorporated by reference in their entirety. In case of a conflict in terminology, the present specification is controlling.

Provided herein according to embodiments of the invention are poly(urea-urethane) polymers that may be useful in treating particular skin ailments and/or protecting skin. Also provided herein are pharmaceutical compositions that may include a poly(urea-urethane) polymer according to an embodiment of the invention. Furthermore, provided herein are methods of using a poly(urea-urethane) polymer and/or a pharmaceutical composition according to an embodiment of the invention to treat skin ailments and/or skin infection. Finally, methods of forming a skin bandage using a poly (urea-urethane) polymer and/or a pharmaceutical composition according to an embodiment of the invention are also provided herein.

I. Definitions

As used herein, the following terms have the meanings provided below:

The term "alkyl" refers to a straight, branched or cyclic hydrocarbon. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl, and the like. "Lower alkyl" is a subset of alkyl and refers to a hydrocarbon group containing from 1 to 4 carbon atoms. Representative examples of lower alkyl include, but are not limited to, methyl, ethyl, n-propyl, iso-propyl, n-butyl, iso-butyl, tert-butyl, and the like. The term "alkyl" is intended to include both substituted and unsubstituted alkyl unless otherwise indicated. Substituted alkyl may be substituted with one or more (e.g., one, two or three) suitable functional groups including, e.g., halo, alkyl, alkoxy, haloalkyl, amino, hydroxyl, aryl, isocyanato, and the like.

The term "alkoxy" refers to the functional group —OR, wherein R is an alkyl, as defined herein.

The terms "aryl" and "arylene" refer to a monovalent or divalent, respectively, monocyclic carbocyclic ring system or a bicyclic carbocyclic fused ring system having one or more aromatic rings. Representative examples of aryl(ene) include, azulenyl(ene), indanyl(ene), indenyl(ene), naphthyl(idene), phenyl(ene), tetrahydronaphthyl(idene), and the like. The term "aryl(ene)" is intended to include both substituted and unsubstituted aryl unless otherwise indicated. Substituted aryl(ene) may be substituted with one or more suitable functional groups (e.g., one, two or three), including, e.g., alkyl and those groups set forth in connection with alkyl above.

The term "poly(urea-urethane) polymer" is meant to refer to (i) poly(urea) polymers and (ii) polymers that include both urea (—NRC(=O)NR'—) and urethane (—NR"C(=O)O—) linkages, wherein R, R' and R" are each independently hydrogen; alkyl, as defined above; or aryl, as defined above. All polymers herein are described according to the monomer units that react to form the polymer, such as, e.g., polyamines, polyols, polyisocyanates, and the like. The term "polymer" will be understood to include polymers, copolymers (e.g., polymers formed using two or more different monomers), oligomers and combinations thereof, as well as polymers, oligomers, or copolymers that can be formed in a miscible blend. The term "pre-polymer" refers to a monomer or system of monomers that have been reacted to an intermediate molecular weight state. This material is capable of further polymerization by reactive groups to a fully cured high molecular weight state. As such, mixtures of reactive polymers with unreacted monomers may also be referred to as pre-polymers. Typically such prepolymers are polymers of relatively low molecular weight, usually between that of the monomer and the film polymer or resin. As such, one of skill in the art will appreciate that monomers react to form the poly(urea-urethane) such that the monomer is no longer present once the polymer is formed. However, in some pharmaceutical compositions described herein, both monomer and polymer may be present in the formulation prior to curing, and after curing, residual monomer may remain in the cured polymer.

The term "polyamine" is meant to refer to compounds having at least two (primary and/or secondary) amine functional groups per molecule.

The term "polyol" is meant to refer to compounds having at least two hydroxyl functional groups per molecule.

The term "polyisocyanate" and "polyisothiocyanate," collectively referred to as "polyiso(thio)cyanate" are meant to refer to compounds having at least two isocyanate or isothiocyanate, respectively, functional groups per molecule.

The terms "pharmaceutical composition" and "medicament" are used interchangeably herein to refer to a composition comprising a therapeutically effective amount of (i) a poly(urea-urethane) polymer according to an embodiment of the present invention, a pharmaceutically acceptable salt thereof and/or monomers thereof; (ii) a pharmaceutically acceptable carrier; and (iii) optionally, other additives.

The term "pharmaceutically acceptable salt" refers to a salt or salts prepared from at least one pharmaceutically acceptable non-toxic acid or base including inorganic acids and bases, and organic acids and bases. Pharmaceutically acceptable salts of compounds according to embodiments of the invention include the acid addition and base salts thereof, and may be made using techniques known in the art, such as, but not limited to, reacting the compound with the desired base or acid. Suitable pharmaceutically acceptable base addition salts for compounds according to embodiments of the present invention include metallic salts (e.g., alkali metal salts and/or alkaline earth metal salts) made from aluminum, calcium, lithium, magnesium, potassium, sodium, and zinc; or organic salts made from lysine, N,N'-dibenzylethyl-enediamine, chloroprocaine, choline, diethanolamine, ethylenediamine, meglumine (N-methylglucamine) and procaine. Suitable non-toxic acids include, but are not limited to, inorganic and organic acids such as acetic, alginic, anthranilic, benzenesulfonic, benzoic, camphorsulfonic, citric, ethenesulfonic, formic, fumaric, furoic, galacturonic, gluconic, glucuronic, glutamic, glycolic, hydrobromic, hydrochloric, isethionic, lactic, maleic, malic, mandelic, methanesulfonic, mucic, nitric, pamoic, pantothenic, phenylacetic, phosphoric, propionic, salicylic, stearic, succinic, sulfanilic, sulfuric, tartaric acid, and p-toluenesulfonic acid. Specific non-toxic acids include hydrochloric, hydrobromic, phosphoric, sulfuric, and methanesulfonic acids. Examples of specific salts thus include xinofoate, hydrochloride mesylate, zinc, potassium, or iron salts. In certain embodiments, both water-soluble and water-insoluble salts will be useful based on the mode of administration.

The term "pharmaceutically acceptable carrier" is used herein to refer to a carrier medium that does not significantly alter the biological activity of the poly(urea-urethane) polymer. The one or more substances of which the pharmaceutically acceptable carrier is comprised typically depends on factors (or desired features for its intended use) of the pharmaceutical composition such as the intended mode of administration, desired physical state (e.g., solid, liquid, gel, suspension, etc.), desired consistency, desired appearance, desired taste (if any), desired pharmacokinetic properties once administered (e.g., solubility, stability, biological half life), desired release characteristics (e.g., (a) immediate release (e.g., fast-dissolving, fast-disintegrating), or (b) modified release (e.g., delayed release, sustained release, controlled release)), and the like. As known to those skilled in the art, a suitable pharmaceutically acceptable carrier may comprise one or substances, including but not limited to, a diluent, water, buffered water, saline, 0.3% glycine, aqueous alcohol, isotonic aqueous buffer; a water-soluble polymer, glycerol, polyethylene glycol, glycerin, oil, salt (e.g., such as sodium, potassium, magnesium and ammonium), phosphonate, carbonate ester, fatty acid, saccharide, polysaccharide, stabilizing agent (e.g., glycoprotein, and the like for imparting enhanced stability, as necessary and suitable for manufacture and/or distribution of the pharmaceutical composition), excipient, preservative (e.g., to increase shelf-life, as necessary and suitable for manufacture and distribution of the pharmaceutical composition), bulking agent (e.g., microcrystalline cellulose, and the like), suspending agent (e.g., alginic acid, sodium alginate, and the like), viscosity enhancer (e.g., methylcellulose), taste enhancer (e.g., sweetener, flavoring agent, taste-masking agent), binder (generally, to impart cohesive quality to a tablet or solid formulation; e.g., gelatin, natural and/or synthetic gums, polyvinylpyrrolidone, polyethylene glycol, and the like), extender, disintegrant (e.g., sodium starch glycolate, sodium carboxymethyl cellulose, starch, and the like), dispersant, coating (generally to impart a surface active agent to a tablet or solid formulation; e.g., polysorbate, talc, silicon dioxide, and the like), lubricant (e.g., magnesium stearate, calcium stearate, sodium lauryl sulphate, and the like), or colorant. Other suitable additives include those described elsewhere herein. As known to those skilled in the art, an active ingredient may be formulated into a pharmaceutical composition using methods and one or more pharmaceutically acceptable carriers well known in the art, taking the desired features of the pharmaceutical composition, as described above, in mind during formulation. Depending on such desired features, typically a pharmaceutical composition may comprise from about 1% by weight to about 80% by weight of poly(urea-urethane), and from about 10% by weight to about 99% by weight of pharmaceutically acceptable carrier.

The term "therapeutically effective amount" refers to that amount of a poly(urea-urethane) polymer according to an embodiment the present invention that is sufficient to prevent, minimize or improve/ameliorate one or more symptoms of one or more of the ailments described herein. Improvement/amelioration may be indicated visually, e.g., reduced redness, via laboratory testing and/or may be indicated by reduced discomfort or irritation to the inflicted subject.

The terms "treat", "treating" and "treatment" means preventing or ameliorating one or more of the ailments described herein. Thus, the terms apply to prophylactic and/or therapeutic applications. The terms also apply to the prevention or amelioration of one or more symptoms of a particular ailment, including the prevention or amelioration of any infection related to the particular ailment.

The term "bacteria," as used herein, includes any organism from the prokaryotic kingdom, including gram positive and gram negative bacteria. These organisms include genera such as, but not limited to, *Agrobacterium, Anaerobacter, Aqualbacterium, Azorhizobium, Bacillus, Bradyrhizobium, Cryobacterium, Escherichia, Enterococcus, Heliobacterium, Klebsiella, Lactobacillus, Methanococcus, Methanothermobacter, Micrococcus, Mycobacterium, Oceanomonas, Pseudomonas, Rhizobium, Staphylococcus, Streptococcus, Streptomyces, Thermusaquaticus, Thermaerobacter, Thermobacillus*, and the like. Exemplary bacteria include those described in United States Patent Application Publication No. 2003/0068808.

The term "virus," as used herein, includes any virus, including double-stranded DNA viruses (e.g., Adenoviruses, Herpesviruses, Poxviruses), single-stranded (—O-sense DNA viruses (e.g., parvoviruses), double stranded RNA viruses (e.g., Reoviruses), single-stranded (+)sense RNA viruses (e.g, Picornaviruses, Togaviruses), single-stranded (−)sense RNA viruses (e.g., Orthomyxoviruses, Rhabdoviruses), single stranded (+)sense RNA having a DNA intermediate in the life-cycle (e.g, Retroviruses), and double stranded DNA with RNA intermediate (e.g., Hepadnaviruses). Exemplary viruses include humanpapilloma virus, herpes simplex virus and poxvirus.

The term "fungus," as used herein, includes any fungus or mold, including arbuscular mycorrhiza, conidiophores, chytridiomycota, blastocladiomycota, neocallimastigomycota, zygomycota and glomeromycota. The term also includes slime molds and water molds. Exemplary fungi include *candida, malassezia furfur, Pityrisporum ovalae*, and dennophytes such as *Trichophyton, Microsporum* and *Epidermophyton*.

II. Poly(Urea-Urethane) Polymers According to Embodiments of the Invention

According to some embodiments of the present invention, provided are poly(urea-urethane) polymers that include (a) a primary and/or secondary polyamine; (b) a polyiso(thio)cyanate and/or a derivative thereof; (c) optionally, a polyol; and (d) optionally, additional comonomers.

(a) Primary and Secondary Polyamines

In some embodiments of the present invention, the poly (urea-urethane) polymer includes an aliphatic primary and/or secondary polyamine. The primary and/or secondary polyamine may also include various other functional groups within the polyamine, including polyether, polyester, polycarbonate and/or polypropylene linkages.

In some embodiments, the polyamine includes a primary diamine that includes at least one polyoxyalkylenediamine. For example, in some embodiments, the polyamine includes a diamine encompassed by Formula 1.

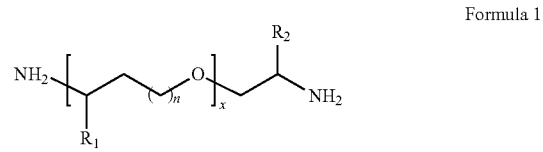

Formula 1 wherein $R_1$ and $R_2$ are each independently hydrogen or alkyl; n is 0 or a positive integer, such as 1, 2, 3 or 4; and x is a positive integer in a range of 1 to 100, and in some embodiments is 1, 2, 3, 4, 5, 10, 50 or 100. Exemplary primary polyoxyalkylenediamines include Jeffamine® D-2000 polyetheramine, manufactured by Huntsman Petrochemical Corporation and Poly-A® 27-2000, manufactured by Arch Chemicals.

In some embodiments, the polyamine includes an aliphatic secondary diamine that includes an N-alkyl polyoxyalkylenediamine. For example, in some embodiments, the polyamine includes an aliphatic secondary amine encompassed by Formula 2.

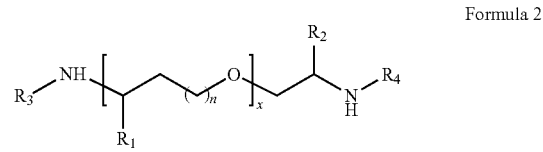

Formula 2 wherein $R_1$ and $R_2$ are each independently hydrogen or alkyl; $R_3$ and $R_4$ are each independently alkyl or aryl; n is 0 or a positive integer, such as 1, 2, 3 or 4; and x is a positive integer in a range of 1 to 100, and in some embodiments is 1, 2, 3, 4, 5, 10, 50 or 100.

In some embodiments of the invention, the primary and/or secondary polyamine included in the poly(urea-urethane) may include an aryl(ene) functional group, such as phenyl (ene), naphthyl(idene) and the like. The primary and/or secondary polyamine may also include various other functional groups, such as polyether, polyester, polycarbonate and/or polypropylene linkages.

In some embodiments, the polyamine includes an aromatic primary diamine, such as a compound encompassed by Formula 3.

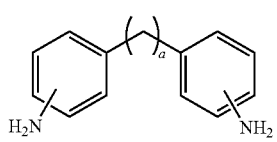

Formula 3 wherein a is a positive integer, such as 1, 2, 3, 4 or 5. In particular embodiments, the primary amine groups are each located on their respective phenyl rings at the para position.

In some embodiments, the polyamine includes an aromatic secondary diamine, such as a compound encompassed by Formula 4.

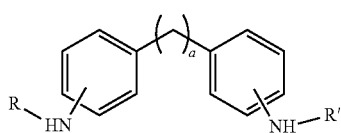

Formula 4 wherein a is a positive integer such as 1, 2, 3, 4 or 5, and R and R' are each independently alkyl or aryl. In particular embodiments, the secondary amine groups are each located on their respective phenyl rings at the para position. Exemplary aromatic secondary diamines include Unilink® 4200, manufactured by Dorf Ketal Chemicals.

As one of ordinary skill in the art will appreciate, mixtures of different types of polyamines may be used in some embodiments of the invention, including mixtures of primary and secondary amines.

(b) Polyisocyanates/Polyisothiocyanates

According to some embodiments of the present invention, a polyiso(thio)cyanate is included in the poly(urea-urethane) polymer. Any suitable polyiso(thio)cyanate may be included in the composition including, for example, aliphatic polyisocyanates, aromatic polyisocyanates, alicyclic polyisocyanates, heterocyclic polyisocyanates and heteraromatic polyisocyanates. Exemplary polyisocyanates include polyaryl polyisocyanates as defined in U.S. Pat. No. 2,683,730; tolylene diisocyanate (also referred to as "TDI"); triphenylmethane-4,4'4"-triisocyanate, benzene-1,3,5-triisocyanate; toluene-2,4,6-triisocyanate; diphenyl-2,4,4'-triisocyanate; hexamethylene diisocyanate; xylylene diisocyanate; chlorophenylene diisocyanate; diphenylmethane-4,4'-diisocyanate; naphthalene-1,5-diisocyanate; xylene-alpha, alpha'-diisothiocyanate; 3,3'-dimethyl-4,4'biphenylene diisocyanate; 3-3'dimethoxy-4,4'-biphenylene diisocyanate; 2',3,3'-dimethyl-4,4'-biphenylene diisocyanate; 5,5'-tetramethyl-4,4'biphenylene diisocyanate; 2,2',5,5'-tetramethyl-4,4'biphenylene diisocyanate, 4,4'methylenebis(phenylisocyanate); 4,4'-sulfonylbis(phenylisocyanate); 4,4'-methylene di-ortho-tolylisocyanate; ethylene diisocyanate; ethylene diisothiocyanate; ethylidene diisocyanate; propylene diisocyanate; butylene diisocyanate; cyclopentylene-1,3-diisocyanate; cyclohexylene-1,4-diisocyanate; cyclohexylene-1,2.diisocyanate, 2,4-tolylene diisocyanate; 2,6-tolylene diisocyanate; 4,4'-diphenylmethane diisocyanate; 2,2-diphenylpropane-4,4'-diisocyanate; p-phenylene diisocyanate; m-phenylene-1,5 diisocyanate; xylylene diisocyanate; 1,4-napthylene diisocyanate; 1,5-naphthylene diisocyanate; diphenyl-4,4'diisocyanate; azobenzene-4,4'-diisocyanate; diphenylsulfone-4,4'-diisocyanate; dichlorohexamethylene diisocyanate; tetramethylene diisocyanate; pentamethylene diisocyanate; hexamethylene diisocyanate; 1-chlorobenzene-2,4-diisocyanate; furfurylidene diisocyanate; triphenyl methane triisocyanate; 1,4-tetramethylene diisocyanate; 1,6-hexamethylene diisocyanate; 2,2,4-trimethyl-1.6-hexamethylene diisocyanate; 1,12-dodecamethylene diisocyanate; cyclohexane-1,3(and -1,4)-diisocyanate; 1-isocyanato-2-isocyanatomethyl cyclopentane; 1-isocyanato-3-isocyanatomethyl-3,5,5-trimethyl-cyclohexane (isophorone diisocyanate or IPDI); bis-(4-isocyanatocyclohexyl)-methane; 2,4'dicyclohexyl-methane diisocyanate; 1,3- and 1,4-bis(isocyanatomethyl)-cyclohexane; bis-(4-isocyanato-3-methyl-cyclohexyl)-methane,α,α,α',α'-tetramethyl-1,3-1-isocyanato-1-methyl-4(3)-isocyanatomethyl cyclohexane; 2,4-, 1,3- and/or 1,4-phenylene diisocyanate; 2,4- and/or 2,6-toluoylene diisocyanate; 2,4- and/or 4,4'-diphenyl-methane diisocyanate; 1,5-diisocyanato naphthalene; aromatic polyisocyanates containing 3 or more isocyanate groups such as 4,4',4"-triphenylmethane diisocyanate, trimethylenediisocyanate, tetramethylene diisocyanate and hexamethylene diisocyanate; xylene diisocyanate; 1,5-napththylene diisocyanate; 1,4-phenylene diisocyanate; 4,4'-'diphenylmethane diisocyanate (also referred to as "MDI") (Dow's ISONATE® 125M); 4,4'4"-triphenylmethane triisocyanate; and 3,3'-dimethyl-4.4'-diphenylmethane diisocyanate; and the like. Aliphatic diisocyanates such as the $C_{36}$ aliphatic diisocyanate derived from the dimer of ricinoleic acid can also be suitably employed and are commercially available, for example, as DD1-1410 (Henkel Corporation, Resin Division, Minneapolis. Minn.). Other examples of polyisocyanates can be found, for example, in *The Development and Use of Polyurethane Products*, E. N. Doyle, McGraw-Hill Book Company, page 27 (1971) and *Polyurethane Handbook*, Gunter Oertel Hauser. Gardner Press (1994).

Mixtures of two or more polyiso(thio)cyanates may also be used. Furthermore, different isomers of the same isocyanate or isothiocyanate may be used. For example, in some embodiments, a mixture (e.g., 80/20 or 65/35 by weight) of 2,4-toluene diisocyanate and 2,6 toluene diisocyanate may be used.

In some embodiments of the invention, the polyiso(thio) cyanates are liquid at ambient temperatures. Liquid polyiso (thio)cyanates may facilitate the production of polymeric products and may obviate the need to melt or dissolve a polyiso(thio)cyanate prior to reacting it. Suitable liquid polyisocyanate materials are known to those of ordinary skill in the art and include, e.g., a liquid polyisocyanate disclosed in U.S. Pat. No. 3,394,164.

Prepolymer polyisocynates of higher molecular weight (e.g., greater than 500 grams per mole) that have been cleanly stripped of low molecular weight diisocynate starting materials may be particularly useful in applications wherein the presence of trace diisocyanate monomers may be undesirable in end use applications, e.g., when trace diisocyanate monomers may cause irritation or sensitization.

In particular embodiments of the invention, the polyisocyanate is MDI or a derivative thereof. MDI is a solid with a melting point of 38° C. and may form significant quantities of insoluble dimers when stored above 40° C. Therefore, so-called "modified" MDI derivatives, which are liquid at room temperature and have a reduced tendency to dimerize, may be used. Modified MDIs include those formed by reacting the diisocyanate with a short polyol in a 2:1 diisocyanate to diol ratio, with a short triol in a 3:1 diisocyanate to triol ratio or by converting part of the mixture to a trifunctional carbodiimide-based diisocyanate trimer having the structure of Formula 5. Such an admixture may be obtained from Dow (Liquid MDI, Isonate 143L).

Formula 5

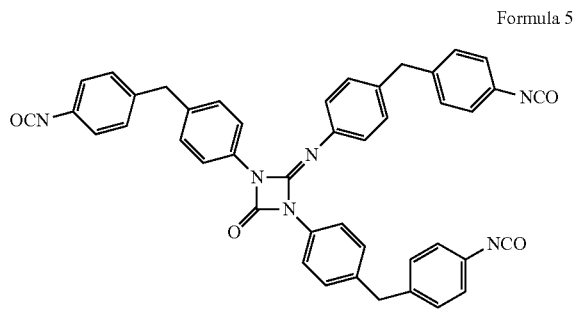

Both of these modifications may provide the MDI with suitable reactivity and a relatively long shelf-life. In some cases, a modified MDI having approximately 2.2 isocyanate groups per molecule may have a shelf life of up to 6 months, in a moisture-controlled environment, and at a temperature of between 25° C. and 35° C.

The MDI may also include mixtures of different isomers, including 2,4 and 2,2 isomers. The 2-substituted configuration is typically less reactive than the 4-substituted configuration. The use of different isomers may affect the polymer architecture of the poly(urea-urethane) polymer, and additionally, when a relatively high percentage of MDI isomers is incorporated into the poly(urea-urethane), a lower molecular weight polymer may result. Furthermore, 2,4- and 2,2-linkages may introduce a "kink" or bend in the polymer chain, which may reduce the tendency of the materials to crystallize. The choice of MDI derivative (e.g., isomer) may affect properties of the solution, the cured film (e.g., curing time), etc. Therefore, the composition of the MDI (or any polyisocyanate/polyisothiocyanate) may be selected as desired for a particular application.

Liquid polyisocyanates may also be formed during the synthesis of MDI. In the production of MDI via the condensation of aniline with formaldehyde, thereby converting the amine groups to the corresponding isocyanate groups, a portion of the initially formed bis-adduct of aniline and formaldehyde may further react with the reaction mixture to form polymeric aniline derivatives that may be converted to isocyanates. Typically, such polymeric derivatives will have a functionality of from about 4 to about 15, and in some cases, about 10 isocyanate groups per molecule. Such polymeric polyiscocyanates may be obtained after removal of pure MDI by distillation. These polyisocyanate products may be used by themselves or in an admixture with pure MDI. For example, the undistilled reaction mixture of pure MDI with the polymeric MDI may be used. Such polymeric MDI products are commercially available under such trade designations as RUBINATE® M, RUBINATE® LF-168 and RUBINATE® LF-209 (Huntsman Polyurethanes, Geisman, La.) and PaPI 27, PaPI 135, PaPI 580 and PaPI 901 (Dow, Kalamazoo, Mich.).

In some embodiments of the invention, the polyiso(thio) cyanate component may be present in the form of a polyiso (thio)cyanate adduct. For example, the polyisocyanate may be present as an adduct that includes isocyanurate, uretidone, biuret, urethane, allophanate, carbodiimide and/or oxadiazinetrione groups. In some embodiments, the polyisocyanate adducts have an average functionality of 2 to 6 and an NCO content of 5 to 30% by weight. The isocyanato-isocyanurates generally have an average NCO functionality of 3 to 3.5 and an NCO content of 5 to 30%, in some embodiments 10 to 25%, and in particular embodiments, 15 to 25% by weight. In some embodiments of the invention, a mixture of polyisocyanate adducts are present, such as a mixture of isocyanurate and allophanate groups.

According to some embodiments of the invention, the polyiso(thio)cyanate component is present as a prepolymer (hereinafter, collectively referred to as "NCO prepolymer"). Such NCO prepolymers may be prepared from any of the previously described polyiso(thio)cyanates and/or polyiso (thio)cyanurate adducts, in combination with an organic compound that is capable of reacting with the polyiso(thio)cyanates and/or polyiso(thio)cyanurate adducts. In some embodiments, such organic compounds include a polyol, e.g., a polyol described herein. In some embodiments, the prepolymer is formed with an organic compound having a number average molecular weight in a range of 400 to 6000, and in some embodiments, in a range of 800 to 3000. Furthermore, in some embodiments, the prepolymer is formed with an organic compound having a number average molecular weight of less than 400. Such molecular weights may be determined by end group analysis (OH number).

With regard to the organic polyisocyanates, the prepolymers and polyisocyanate adducts, reference is made to U.S. Pat. No. 5,516,873 and U.S. Pat. No. 6,515,125 and references contained therein.

As one of skill in the art would readily appreciate, mixtures of any of the above polyiso(thio)cyanates, including derivatives thereof, may be incorporated in the poly(urea-urethane) polymers described herein. In particular embodiments, mixtures of MDI and derivatives thereof are utilized, including those mixtures marketed under the tradename Lupranate® (e.g., Lupranate® 81 and 218), manufactured by BASF Aktiengesellschaft.

(c) Polyols

In some embodiments of the invention, a polyol is not used to form the poly(urea-urethane) polymer. In such a case, a poly(urea) may be formed. However, in some embodiments of the invention, a polyol may be incorporated into the polymer and a poly(urea-urethane) polymer may be formed. For example, in some embodiments, an aliphatic polyol is included in the poly(urea-urethane) polymer. In some embodiments, the aliphatic polyol includes a diol having a structure encompassed by Formula 5.

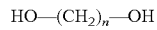
HO—(CH$_2$)$_n$—OH
Formula 5 wherein n is a positive integer. In some embodiments n is a positive integer in a range of 1 to 6, in some embodiments in a range of 5 to 9, and in some embodiments, n is 1, 2, 3 or 4. Exemplary polyols include ethylene glycol, propylene glycol and butylene glycol (such as 1,3-, 1,4- and 2,3-butylene glycol).

In some embodiments, the polyol includes a diol having a structure encompassed by Formula 6.

Formula 6 wherein p is a positive integer, and R and R' are each independently hydrogen or alkyl. In some embodiments, p is an integer in a range of 1 to 100, in particular embodiments, p is 1, 2 or 3; and in particular embodiments p is 4 or more. Exemplary polyols include polyethylene glycol and polypropylene glycol having various molecular weights (e.g., 200, 400, 600, 1000). Other polyols include trimethylol propane and those marketed under the name Multranol® (e.g., Multranol® 4012), manufactured by Bayer Material Science.

As one of ordinary skill in the art will appreciate, mixtures of polyols may be used in some embodiments of the invention. In particular embodiments, ethylene glycol and propylene glycol are provided in equal amounts. Additionally, as described above, in particular embodiments, polyols may be used to form prepolymers with the polyiso(thio)cyanates.

(d) Additional Comonomers

In some embodiments of the invention, other comonomers may be reacted with the polyamines, (optionally) polyols and poly(iso)thiocyanates and become incorporated into the poly (urea-urethane) polymer. For example, in some embodiments, siloxanes may be incorporated into the poly(urea-urethane). Siloxane segments may impart additional water resistance and flexibility to the coating. Additionally, siloxanes such as poly(dimethyl siloxane) may be used to treat burns, and so incorporating such materials into the poly(urea-urethane) may provide additional beneficial properties to the coatings. Such siloxane segments may be introduced into the poly(urea-urethane) by incorporating siloxane-containing polyols, polyamines, polyisocyanates, alcohols, amines and isocyanates into the reaction mixture. Exemplary polyols and polyamines may be found in U.S. Pat. Nos. 3,384,599, 4,737, 558, 4,962,178, 4,942,212, 5,221,724, 5,430,121, 5,589,563 and 5,196,458.

Fluorinated comonomers may also be included in the poly (urea-urethane) polymer, according to some embodiments of the invention. Fluorinated segments incorporated into the polyurea/urethane polymer may impart additional water resistance/repellency, and may also impart hydrocarbon resistance and/or low surface tension materials, in embodiments wherein such characteristics are desirable. Such fluorinated segments may be introduced into the poly(urea-urethane) by incorporating fluorine-containing polyols, polyamines, polyisocyanates, alcohols, amines and isocyanates into the reaction mixture. Such fluorinated comonomers are known to those skilled in the art. Exemplary fluorinated comonomers include those described in U.S. Pat. No. 5,453, 540, EP 0646796B1 and WO 2007/011593A1.

(e) Synthesis of the Poly(Urea-Urethane) Polymers

The poly(urea-urethane) polymers according to embodiments of the invention may be prepared using any suitable technique known to those of skill in the art. As such, the polymerization methods may be homogenous or heterogeneous, including, e.g., solution, precipitation, suspension and emulsion polymerization methods. Such polymerization techniques are described in further detail in *Principles In Polymerization*, by George Odian (Wiley-Interscience, 4$^{th}$ ed., 2004). Specific examples of heterogeneous polymerizations including isocyanate-based polymerizations to form polyureas and polyurethanes, and related polymers, may be found in U.S. Pat. No. 4,107,256 and U.S. Pat. No. 6,197,878.

Depending on the polymerization method utilized, additional surfactants or stabilizers may necessary in order to prevent agglomeration or precipitation. Such additives are well-known to those of skill in the art and may be chosen so as to be chemically incorporated (e.g., covalently linked) into the poly(urea-urethane) polymer. Such additives may also be chosen so as to avoid reactivity with the monomers employed in the formulation.

The order and rate of adding the polyamines, polyols, additional monomers and polyiso(thio)cyanates may substantially alter the final architecture of the resulting prepolymer. As such, various preparations may be used to achieve the desired polymer structure. In some embodiments of the invention, the polyamine, polyol, polyisocyanate and additional comonomers may be added to a solvent at one time, or may be added in a particular order. Toward this end, in some embodiments, one or more of the monomers may be added to the reaction mixture in a continuous addition mode (e.g., via batch, semi-batch or continuous polymerization methods). Additionally, under some circumstances, specific combinations of monomers, such as polyamines and polyisocyanates, or polyols and polyisocyanates, may be reacted in a first step to form a polymeric isocyanate prepolymer. Such prepolymer synthesis may allow for the further control of polymer architecture, solubility or allow for tailoring of the properties of the final polymer surface. In particular embodiments of the invention, all polyamine and polyol monomers are added to a solvent in a first step and then the isocyanate is added in a second step. In such circumstances, the isocyanate will react and incorporate the polyamines and polyols in a statistical fashion according to their relative reactivity.

Catalysts may be added to the polymerization mixture in order to increase or otherwise control polymerization or curing rates. Such catalysts are known to those of skill in the art, and include, e.g., the catalysts described in U.S. Pat. No. 4,960,620. The polyamines and polyols may react with the polyisocyanate at room temperature. However, in some embodiments, the reaction medium can be heated to facilitate the reaction.

III. Pharmaceutical Compositions According to Embodiments of the Invention

In some embodiments of the invention, provided are pharmaceutical compositions that include (a) at least one poly (urea-urethane) polymer according to an embodiment of the present invention, a pharmaceutically acceptable salt thereof and/or monomers thereof; (b) a pharmaceutically acceptable carrier; and (c) optionally, other additives.

Poly(urea-urethane) Polymers

Any of the polyurea or poly(urea-urethane) polymers described herein may be included in pharmaceutical compositions according to embodiments of the invention. In addition, monomers that will form such polymers upon curing may also be included in pharmaceutical compositions according to embodiments of the invention. Furthermore, mixtures of any polyurea polymer, poly(urea-urethane) polymer and monomers thereof may also be present in pharmaceutical compositions according to embodiments of the invention.

(b) Pharmaceutically Acceptable Carrier/Solvent

According to some embodiments of the invention, pharmaceutical poly(urea/polyurethane) compositions include a pharmaceutically acceptable carrier. In some embodiments, the pharmaceutically acceptable carrier is a solvent that can completely dissolve the monomers (polyamines and polyiso (thio)cyanates, and optionally, polyols and additional comonomers). Additionally, in some embodiments, the pharmaceutically acceptable carrier will reduce the reaction between the reactive groups in the poly(urea-urethane) monomers and/or reduce or prevent the poly(urea-urethane) from solidifying or gelling until the desired time, such as when the solvent is removed from the solution, e.g., via evaporation.

In particular embodiments of the invention, the pharmaceutically acceptable carrier includes a solvent such as an aldehyde; ketone; ester; ortho, meta, or para-dimethylbenzene; N-methylpyrrolidone; Solvesso solvent; a hydrocarbon solvent, such as a petroleum hydrocarbon solvent; a lactone; a siloxane, or a mixture of any of the above. Additional solvents may be found in U.S. Patent Publication Nos. 2006/021627, and U.S. Publication No. 2006/008856A1 and U.S. Pat. Nos. 3,577,516, 4,987,893, 5,103,812, 6,458,376, 6,994,863, 5,874,481.

In some embodiments, an aldehyde or ketone solvent has a structure encompassed by Formula 7.

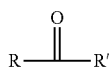

Formula 7 wherein R and R' are each independently selected from hydrogen and alkyl. In some embodiments, the alkyl may include 1, 2, 3 or 4 carbon atoms. In some embodiments, R and R' together form a ring, such as a five or six membered ring. Exemplary ketones include acetone, methylethylketone (MEK), methylisobutylketone and N-methylcyclohexanone. Exemplary aldehydes include acetaldehyde, propionaldehyde, butyraldehyde and isobutyraldehyde.

As an additional example, in some embodiments, an ester solvent has a structure encompassed by Formula 8.

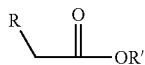

Formula 8 wherein R is hydrogen, alkyl (such as an alkyl including 1, 2, 3 or 4 carbon atoms) or alkoxy (such as an alkoxy that includes 1, 2, 3 or 4 carbon atoms); and R' is an alkyl group (such as an alkyl that includes 1, 2, 3 or 4 carbon atoms). In some embodiments, R and R' together form a ring, such as a ring that includes 2, 3, 4 or 5 carbon atoms. Exemplary ester solvents include methyl acetate, ethyl acetate, butyl acetate, and methyl propyl acetate.

In particular embodiments of the invention, siloxane-based solvents, such as hexamethyldisiloxane, pentamer cyclomethicone tetramer cyclomethicone and mixtures thereof can be employed in poly(urea-urethane) compositions of the invention. Other suitable siloxane solvents are described in U.S. Publication No. 2007/0041935 to Salamone et al., U.S. Pat. No. 6,280,752 to Panin, U.S. Pat. No. 5,582,815 to Appino and U.S. Pat. No. 5,738,857 to Sejpka.

(c) Other Additives/Formulations

According to some embodiments of the invention, the compositions described herein may include other additives, including, but not limited to, catalysts, UV absorbers, fillers, plasticizers, blowing agents, rheology modifiers, viscosity enhancers, adhesion promoters and those described in U.S. Patent Application Publication No. 2006/0216267. Other additives are described elsewhere herein.

In particular embodiments, formulations of the present invention are suitable for topical administration for medical use and use in personal care and/or hygiene (e.g., soaps, skin creams and/or lotions, soaps, cleansers, shampoos, wipes, towelettes, gels, etc.). In other embodiments, the formulations exist in the form of a gel, emulsion, lotion or cream that can be readily used to treat the desired ailment. In still further embodiments, the formulations can be applied to the skin directly or to bandages for wound management.

In particular embodiments, topical compositions may include the poly(urea-urethane) polymer, salts thereof and/or monomers thereof with vitamin E, vitamin A, conjugated linoleic acid, and essential fatty acids. The topical compositions disclosed herein are suitable for topical application to mammalian skin. As described above, the carrier can be in a wide variety of forms, such as sprays, emulsions, mousses, liquids, creams, oils, lotions, ointments, gels and solids. In the case of a solution, it can be lyophilized to a powder and then reconstituted immediately prior to use. For dispersions and suspensions, appropriate carriers and additives include aqueous gums, celluloses, silicates or oils.

In particular embodiments, suitable pharmaceutically acceptable topical carriers include, but are not limited to, water, glycerol, alcohol, propylene glycol, fatty alcohols, triglycerides, fatty acid esters, and mineral oils. Suitable topical cosmetically acceptable carriers include, but are not limited to, solutions, emulsions, dispersions, suspensions, syrups, elixirs, and the like with suitable carriers and additives being water, alcohols, oils, glycols, preservatives, flavoring agents, coloring agents, suspending agents, petroleum jelly, petrolatum, mineral oil, vegetable oil, animal oil, organic and inorganic waxes, such as microcrystalline, paraffin and ozocerite wax, natural polymers, such as xanthanes, gelatin, cellulose, collagen, starch or gum arabic, synthetic polymers, alcohols, polyols, and the like. Preferably, because of its non-toxic topical properties, the pharmaceutically and/or cosmetically-acceptable carrier is substantially miscible in water. Such water miscible carrier compositions can also include sustained or delayed release carriers, such as liposomes, microsponges, microspheres or microcapsules, aqueous based ointments, water-in-oil or oil-in-water emulsions, gels and the like.

In addition to liquids, the compositions according to embodiments of the invention may be provided in an aerosol or non-aerosol spray. The aerosol spray, whether formed from solid or liquid particles, can be produced by the aerosol generator. Any suitable propellant may be used in carrying out the present invention. Particularly, formulations to be applied in spraying forms such as dispersible concentrates or powders may contain surfactants such as wetting and dispersing agents, e.g., the condensation product of formaldehyde with naphthalene sulphonate, an alkylarylsulphonate, a lignin sulphonate, a fatty alkyl sulphate, and ethoxylated alkylphenol and an ethoxylated fatty alcohol.

In particular embodiments, formulations suitable for topical application to the skin can take the form of an ointment, cream, lotion, paste, gel, spray, aerosol, or oil. Carriers that can be used include petroleum jelly, lanoline, polyethylene glycols, alcohols, transdermal enhancers, and combinations of two or more thereof.

Formulations suitable for rectal administration can be presented as suppositories. These can be prepared by admixing the compounds described herein with one or more conventional excipients or carriers, for example, cocoa butter, polyethylene glycol or a suppository wax, which are solid at room temperature, but liquid at body temperature and therefore melt in the rectum cavity and release the polymers and compositions described herein.

(d) "Single Component" Formulations

According to some embodiments of the present invention, pharmaceutical compositions may be formulated as single component formulations. The term "single component," as used herein, refers to a "one pot" formulation that does not require a curing agent or accelerant in order to cure the formulation and form a film. Instead, the formulation can be administered to a subject in need thereof in the manner in which it is stored, without combining or mixing the formulation with another component.

Such single component formulations may be obtained by reducing the reactivity of the components in the formulation. In order to achieve this, the single component formulations can be prepared by judicious selection of the appropriate amounts of each component, as well as the appropriate amount and type of solvent. For example, in some embodiments, the solvent is present in the formulation in an amount in a range of about 10 weight percent and about 95 weight percent. In particular embodiments, the solvent is present in the formulation in an amount in a range of about 50 weight percent and about 90 weight percent. Furthermore, in some embodiments, the polyamine component includes a secondary polyamine in an amount in a range of about 0.5 weight percent and 5 weight percent. Additionally, the particular polyiso(thio)cyanates included may also affect the reactivity and so particular polyiso(thio)cyanates are useful for achieving single component formulations. For example, modified MDI polyisocyanates having higher percentages (e.g., in a range of 10% and 40%) 2-substituted phenyl isocyanate groups, such as modified MDI polyisocyanates including Lupranate® 218 and Lupranate® 81, may be used.

In some embodiments, the amount of solvent employed is that which is sufficient to dissolve a first set of reactants (polyamines and optionally polyols and any additional comonomers) with the polyiso(thio)cyanate second reactant, and allow for the reaction product thereof, i.e., the poly(urea-urethane) to remain in solution without precipitation or gelling. Typically, the amount of solvent employed is about 10 to 80% of the total reaction solution volume. The amount of solvent is adjusted depending upon the viscosity desired for specific application requirements. Typically, the reaction product viscosity will range from about 0.05 centipoise to about 1800 centipoise at room temperature.

According to some embodiments of the invention, the single component poly(urea-urethane) compositions can be stored for a relatively long period of time, e.g. greater than 3 months at 25° C. without exhibiting precipitation or gelling, greater than 6 months at 25° C. without precipitation or gelling, or even greater than 1 year at 25° C. without precipitation or gelling. Accordingly, such compositions can be applied in any manner that allows for the removal of at least a portion of the pharmaceutically acceptable carrier, leading to the formation of a solid, cured poly(urea-urethane) material.

While the process and the single pot formulation permits the production of polymeric materials without the use of blocking agents, end-capping chemical modifications or thermally activated catalysts, e.g. caprolactum, B-carbonyl compounds (such as ethyl aceto acetate, ethyl malonate), alcohols and oximes; polymerization additives of various types employed in the manufacture of polymeric products can desirably be employed. For example, such polymerization agents as catalysts, ultraviolet absorbers, fillers, plasticizers, blowing agents, etc., can be employed where desired. Further information on such additives may be found in U.S. Patent Publication No. 2006/0216267 and elsewhere herein.

III. Methods Of Using Poly(Urea-Urethane) Polymers And Pharmaceutical Compositions According to Embodiments of the Invention Provided herein, according to some embodiments of the invention, are methods of treating particular skin ailments and infections. In some embodiments, the methods include administering to a subject a poly(urea-urethane) polymer according to an embodiment of the invention to a subject. In some embodiments, methods include administering to a subject in need thereof, a therapeutically effective amount of a pharmaceutical composition according to an embodiment of the invention. In particular embodiments, administering includes applying a poly(urea-urethane) or pharmaceutical composition according to an embodiment of the invention to the affected skin. Treatment of the skin ailments and infections described herein may improve symptoms such as pain, discomfort, swelling, and/or infection. The particular skin ailments and infections include those described herein.

In some embodiments of the invention, provided are methods of treating rashes, include those caused by contact with rash-causing source, such as poison sumac, poison oak, poison ivy.

In some embodiments of the invention, provided are methods of treating bites or stings, such as from bees, yellow jackets, wasps, brown recluse, spiders, mosquitoes, cats and dogs.

In some embodiments of the invention, provided are methods of treating burns, for example, those being second degree or less, including sun burns.

In some embodiments of the invention, provided are methods of treating rosacea.

In some embodiments of the invention, provided are methods of treating sores, such as bedsores.

In some embodiments of the invention, provided are methods of treating Herpes sores.

In some embodiments of the invention, provided are methods of treating Kaposi's sarcoma and other skin ailments associate with HIV and/or AIDS.

In some embodiments of the invention, provided are methods of treating scarring, such as from surgery or keloid scarring.

In some embodiments of the invention, provided are methods of treating warts, such as plantar warts.

In some embodiments of the invention, provided are methods of treating hemorrhoids and anal sphincter muscle tears.

In some embodiments of the invention, provided are methods of treating cuts and scrapes.

In some embodiments of the invention, provided are methods of treating a bacterial infection of the skin, in which the infection is caused or exacerbated by any type of bacteria. In some embodiments, the bacterial infection is caused by or exacerbated by at least one of the following bacteria: methicillin-susceptible, methicillin-resistant, vancomycin-susceptible and vancomycin-resistant staphylococci (including *Staphylococcus aureus, S. epidermidis, S. haemolyticus, S. hominis, S. saprophyticus*, and coagulase-negative staphylococci), glycopeptide intermediary-susceptible *S. aureus* (GISA), penicillin-susceptible and penicillin-resistant streptococci (including *Streptococcus pneumoniae, S. pyogenes*,

*S. agalactiae, S. avium, S. bovis, S. lactis, S. sangius* and Streptococci Group C, Streptococci Group G and viridans streptococci), enterococci (including vancomycin-susceptiple and vancomycin-resistant strains such as *Enterococcus faecalis* and *E. faecium*), *Clostridium difficile, C. clostridiiforme, C. innocuum, C. perfringens, C. ramosum, Haemophilus influenzae, Listeria monocytogenes, Cornybacterium jeikeium, Bifidobacterium* spp., *Eubacterium aerofaciens, E. lentum, Lactobacillus acidophilus, L. casei, L. plantarum, Lactococcus* spp., *Leuconostoc* spp., *Pediococccus, Peptostreptococcus anaerobius, P. asaccorolyticus, P. magnus, P. micros, P. prevotii, P. productus, Propionibacterium acnes, Actinomyces* spp., *Moraxella* spp. (including *M. catarrhalis*) and *Escherichia* spp. (including *E. coli*), mycobacterium (*Mycobacterium tuburculosis, mycobacterium leprae, Mycobacterium avium complex, Mycobacterium avium* subspecies *paratuberculosis, Mycobacterium palustre, Mycobacterium phlei, Mycobacteriaum smegmatis*), *Pseudomonas aeriginosa, micrococcus luteus* and *Serratia marcesens.*

In some embodiments of the invention, the bacterial infection is treated with a composition according to an embodiment of the invention in combination with at least one other antibacterial, antiviral or antifungal agent. The at least one other antibacterial, antiviral or antifungal agent may be administered topically, or by any other route of administration (e.g, oral, via injection, etc.). Furthermore, the composition according to an embodiment of the invention and the at least one other antibacterial, antiviral or antifungal agent may be used simultaneously or sequentially. Exemplary antibacterial agents include, but are not limited to, penicillins and related drugs, carbapenems, cephalosporins and related drugs, erythromycin, aminoglycosides, bacitracin, gramicidin, mupirocin, chloramphenicol, thiamphenicol, fusidate sodium, lincomycin, clindamycin, macrolides, novobiocin, polymyxins, rifamycins, spectinomysin, tetracyclines, vanomycin, teicoplanin, streptogramins, anti-folate agents including sulfonamides, trimethoprim and its combinations and pyrimethamine, synthetic antibacterials including nitrofurans, methenamine mandelate and methenamine hippurate, nitroimidazoles, quinolones, fluoroquinolones, isoniazid, ethambutol, pyrazinamide, para-aminosalicylic acid (PAS), cycloserine, capreomycin, ethionamide, prothionamide, thiacetazone, viomycin, eveminomycin, glycopeptide, glyclyclycline, ketolides, oxazolidinone; imipenen, amikacin, netilmicin, fosfomycin, gentamycin, ceftriaxone, Ziracin, LY 333328, CL 331002, HMR 3647, Linezolid, Synercid, Aztreonam, and Metronidazole, Epiroprim, OCA-9983, GV-143253, Sanfetrinem sodium, CS-834, Biapenem, A-99058.1, A-165600, A-179796, KA 159, Dynemicin A, DX8739, DU 6681, Cefluprenam, ER 35786, Cefoselis, Sanfetrinem celexetil, HGP-3 1, Cefpirome, HMR-3647, RU-59863, Mersacidin, KP 736, Rifalazil, Kosan, AM 1732, MEN 10700, Lenapenem, BO 2502A, NE-1530, PR 39, K130, OPC 20000, OPC 2045, Veneprim, PD 138312, PD 140248, CP111905, Sulopenem, ritipenam acoxyl, RO-65-5788, Cyclothialidine, Sch-40832, SEP-132613, micacocidin A, SB-275833, SR-15402, SUN A0026, TOC 39, carumonam, Cefozopran, Cefetamet pivoxil and T 3811.

In some embodiments of the invention, provided are methods of treating a viral infection of the skin, in which the infection is caused or exacerbated by any type of virus.

In some embodiments, the infection is caused or exacerbated by at least one the following viruses: humanpapilloma virus, herpes simplex virus and poxvirus. In some embodiments, the viral infection is treated with a composition according to an embodiment of the invention in combination with at least one other antibacterial, antiviral or antifungal agent. The at least one other antibacterial, antiviral or antifungal agent may be administered topically, or by any other route of administration (e.g, oral, via injection, etc.). Furthermore, the composition according to an embodiment of the invention and the at least one other antibacterial, antiviral or antifungal agent may be used simultaneously or sequentially.

In some embodiments of the invention, provided are methods of treating a fungal infection of the skin, in which the infection is caused or exacerbated by any type of fungus. In particular embodiments, the infection is caused or exacerbated by at least one of *candida, malassezia furfur, pityrisporum ovalae*, and dermophytes such as *Trichophyton, Microsporum* and *Epidermophyton*. In some embodiments of the invention, the fungal infection is treated with a composition according to an embodiment of the invention in combination with at least one other antibacterial agent, antiviral or antifungal agent. The at least one other antibacterial, antiviral or antifungal agent may be administered topically, or by any other route of administration (e.g., oral, via injection, etc.). Furthermore, the composition according to an embodiment of the invention and the at least one other antibacterial, antiviral or antifungal agent may be used simultaneously or sequentially.

In some embodiments of the invention, provided are methods of forming a bandage on a portion of the skin of a subject. The methods include providing a composition according to an embodiment of the invention to the skin; and allowing the composition to cure on the skin.

As one of skill in the art will understand, one or more skin ailments or infections (e.g., bacterial, viral and/or fungal) may be present at one time, and one or more compositions according to an embodiment of the invention, optionally in combination with at least one other antibacterial, antiviral or antifungal agent, may be used to treat one, some or all of the skin ailments and/or infections. In addition, in some embodiments, a skin bandage formed by a method described herein may also act to treat a skin ailment and/or infection of the skin in contact with the skin bandage.

Subjects suitable to be treated include, but are not limited to, avian and mammalian subjects. Mammals of the present invention include, but are not limited to, canines, felines, bovines, caprines, equines, ovines, porcines, rodents (e.g. rats and mice), lagomorphs, primates, humans, and the like, and mammals in utero. Any mammalian subject in need of being treated according to the present invention is suitable. Human subjects are preferred. Human subjects of both genders and at any stage of development (i.e., neonate, infant, juvenile, adolescent, adult) can be treated according to the present invention.

Illustrative avians according to the present invention include chickens, ducks, turkeys, geese, quail, pheasant, ratites (e.g., ostrich) and domesticated birds (e.g., parrots and canaries), and birds in ovo.

The invention can also be carried out on animal subjects, particularly mammalian subjects such as mice, rats, dogs, cats, livestock and horses for veterinary purposes, and for drug screening and drug development purposes.

The amount of a composition to be applied, will depend on various factors such as the compound employed in the formulation, the purpose of the treatment (prophylactic or therapeutic), the type of ailment to be treated and the application time.

Any suitable method of administering a poly(urea-urethane) or pharmaceutical composition according to an embodiment of the invention may be used. In some embodiments, the poly(urea-urethane) or pharmaceutical composition may be applied topically to the skin. For example, the poly(urea-urethane) or pharmaceutical composition may be present in a liquid, cream, lotion, emulsion or other formulation, and the such formulation may be placed directly on the skin, either via hand application, via an applicator, via a spray or aerosol, or via any known method of applying medicaments to the skin. For rectal tears, a suppository may be used to apply the polymers and compositions according to embodiments of the invention.

In some embodiments of the invention, pretreating skin or tissue prior to the application of a pharmaceutical composition according to an embodiment of the invention may be advantageous. For example, in situations (e.g., burn treatment) when strong adhesion of the polymer film to the tissue may be undesirable, pretreating the skin with a cleaning solution that incorporates a low surface energy surfactant capable of reacting with the residual isocyanate groups in the poly (urea-urethane), may reduce the reaction of the isocyanate groups with the tissue, thereby reducing adhesion. Conversely, in situations when strong adhesion of the poly(urea-urethane) may be desirable (such as in wound closure/skin bandage), pretreating the skin with a cleaning solution that removes compounds that are capable of reacting with the isocyanate functionalities in the poly(urea-urethane) may allow for the isocyanate functionalities to react with amine and hydroxyl functionalities in the skin or tissue, thereby promoting adhesion. Additionally, compounds such as carboxylic acids (e.g., fatty acids) that are known to promote/catalyze isocyanate-based curing reactions can also be used in pretreating and/or cleaning of the skin. Other compounds that may promote or provide control over adhesion of the poly(urea-urethane) film when used in pretreatment include polymers or monomers that include alcohol, amine or other nucleophilic groups capable of reacting with isocyanate functionality. Examples of such compounds include poly(vinyl alcohol), poly(vinyl acetate), poly(vinyl amine), poly(vinyl acetamide) and their copolymers.

In some embodiments, a particular poly(urea-urethane) or pharmaceutical composition may be useful for more than one of the skin ailments described above. Furthermore, in some embodiments, the poly(urea-urethane) or pharmaceutical composition may be useful as both a polymeric skin bandage and a treatment for at least one of the skin ailments described herein.

The present invention will now be described with reference to the following examples. It should be appreciated that these examples are for the purpose of illustrating aspects of the present invention, and do not limit the scope of the invention as defined by the claims.

EXAMPLES

For each of the following examples, the reagents are added in the order given with stirring for approximately 5 minutes in between reagent additions. The MDI is added last and is added slowly with stirring. The reactions were maintained at room temperature, ca. 70° C., throughout the reaction. After isocynate addition was complete, the reactions were stirred for approximately 10 minutes and then transferred to sample jars for storage prior to being characterized using a combination of High Performance Liquid Chromatography (HPLC), Gel Permeation Chromatography (GPC), Gel Permeation Chromatography with Multi Angle Light Scattering detection (GPC-MALS), Nuclear Magnetic resonance (NMR) Spectroscopy to Fourier Transform Infra Red (FT-IR) Spectroscopy to determine molecular weight, verify chemical structure and verify reaction completion.

Example 1

| | |
|---|---|
| Acetone | 850 ml |
| Methyl Ethyl Ketone | 100 ml |
| Polyetheramine; D-2000 | 60.0 ml |
| Secondary Diamine; UOP 4200 | 15.0 ml |
| Polyether Polyol; Multranol 4012 | 20.0 ml |
| Ethylene Glycol | 5.0 ml |
| Propylene Glycol | 5.0 ml |
| MDI Lupranate 5143 | 32.0 ml |

The resulting product was a clear, off white solution from which a small amount of white solid precipitated and settled to the bottom of the reaction flask. FT-IR spectroscopy and NMR spectroscopy were used to validate structure and showed that only a small portion of isocynate groups are present in the reactive prepolymer. GPC characterization resulted in polystyrene equivalent number average molecular weight of 1,990 g/mol, weight average molecular weight of 6,910 g/mol and polydispersity index of 3.5. No peaks corresponding to residual starting material were observed in the chromatogram.

Example 2

| | |
|---|---|
| Acetone | 212.5 ml |
| Methyl Ethyl Ketone | 25 ml |
| Polyetheramine; D-2000 | 15.0 ml |
| Secondary Diamine; UOP 4200 | 3.75 ml |
| Polyether Polyol; Multanol 4012 | 5.0 ml |
| Ethylene Glycol | 1.25 ml |
| Propylene Glycol | 1.25 ml |
| MDI; Lupranate 81 | 8.0 ml |

The resulting product was a clear, off white solution from which a small amount of white solid precipitated and settled to the bottom of the reaction flask. FT-IR spectroscopy and NMR spectroscopy were used to validate structure and showed that only a small portion of isocyanate groups are present in the reactive prepolymer. GPC characterization resulted in polystyrene equivalent number average molecular weight of 1,960 g/mol, weight average molecular weight of 9120 g/mol and polydispersity index of 4.6. No peaks corresponding to residual starting material were observed in the chromatogram.

Example 3

Additional

| | |
|---|---|
| Acetone | 212.5 ml |
| Methyl Ethyl Ketone | 25 ml |
| Polyetheramine; D-2000 | 15.0 ml |
| Secondary Diamine; UOP 4200 | 3.75 ml |
| Polyether Polyol; Multanol 4012 | 5.0 ml |
| Ethylene Glycol | 1.25 ml |
| Propylene Glycol | 1.25 ml |
| MDI; Lupranate 81 | 8.0 ml |

The resulting product was a clear, off white solution from which a small amount of white solid precipitated formed and settled to the bottom of the reaction flask. FT-IR spectroscopy and NMR spectroscopy were used to validate structure and showed that only a small portion of isocynate groups are present in the reactive prepolymer. GPC characterization resulted in polystyrene equivalent number average molecular weight of 1,740 g/mol, weight average molecular weight of 3,110 g/mol and polydispersity index ($M_w/M_n$) of 1.8. No peaks corresponding to residual starting material were observed in the chromatogram.

Example 4

In this example, the polyetheramine, D-2000, was first dissolved in a mixture of 400 ml acetone and 50 ml Methyl ethyl ketone. The MDI, Lupranate 5143, 32.0 ml was then added slowly in order to form a polyether amine prepolymer adduct. The remaining acetone and Methy Ethyl ketone are placed in a second reaction flask and the remaining reagents added in turn with stirring. Once the remaining co-monomers were all dissolved the polyetheramine/MDI prepolymer aduct was added slowly to the second reaction flask. The resulting formulation was clear with a slightly yellow tint.

| | |
|---|---|
| Acetone | 850 ml |
| Methyl Ethyl Ketone | 100 ml |
| Polyetheramine; D-2000 | 60.0 ml |
| Secondary Diamine; UOP 4200 | 15.0 ml |
| Polyether Polyol; Multranol 4012 | 20.0 ml |
| Ethylene Glycol | 5.0 ml |
| Propylene Glycol | 5.0 ml |
| MDI Lupranate 5143 | 32.0 ml |

Example 5

A formulation according to Example 1 was carried out by pre-reacting Lupranate 5143 and polyether diamine D-2000 in 400 ml of acetone. The resulting solution was then added slowly to the remaining ingredients. A cloudy poly(urethane-urea) solution resulted.

Example 6

A formulation according to Example 1 was carried out, except that MEK was replaced by an equal amount of acetone.

Example 7

A formulation according to Example 1 was carried out, except that one-half of the ethylene glycol and one half of the propylene gloyol were each replaced with a stoichiometrically equivalent amount of polyetherdiamine D-2000.

Example 8

A poly(urea-urethane) formulation prepared according to Example 1 was evaluated for drug delivery potential using in vitro release testing (IVRT) with hydrocortisone medicament. FIG. 1 shows that a film formed from a single application of the formulation, allows hydrocortisone to readily pass through it. This result demonstrates that the poly(urea-urethane) film allows transport of medicaments.

Example 9

Figure 2:
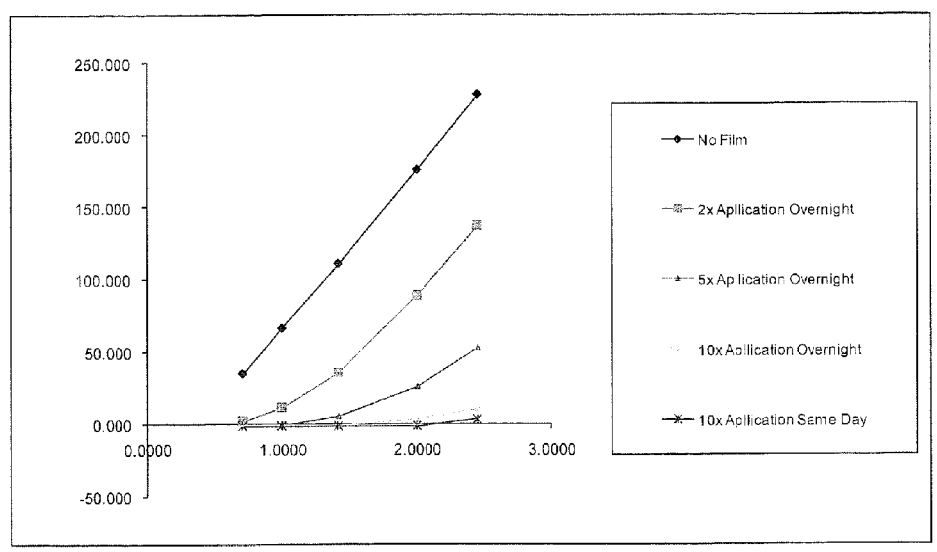
FIG. 2 is a graph illustrating the release rate of a formulation comprising Example 1 and hydrocortisone medicament.

A poly(urea-urethane) formulation prepared according to Example 1 with a hydrocortisone medicament was painted on a membrane surface 2×, 5×, and 10× in 5 minute intervals. The resulting films were evaluated using in vitro release testing (IVRT). Results are shown in FIG. 2. The release of hydrocortisone is predictable and is inversely proportional to the number of applications (and hence film thickness). Thus the release rate of the drug can be controlled by film thickness. These results indicate that the polymer film can incorporate an agent (drug) into its matrix and release it at a constant rate.

Example 10

Water vapor transmission testing was conducted on films cast from a poly(urea-urethane) formulation prepared according to Example 1. Tests were carried out in accordance with test method ASTM E 96/E 96M-05 as follows: Aluminum cups were filled with water to within 19±6 mm of the top, and the sample films were sealed across the cup mouth. Three replicates of each specimen were run. The samples were placed in a sealed chamber with a saturated solution of magnesium nitrate to maintain a controlled humidity. The temperature and humidity were recorded with a solid state sensor, and the cups were weighed periodically (every three and four days, alternately) until a steady rate for mass loss was observed. The average temperature over the testing was approximately 23° C., and the average humidity in the chamber was 74%.

The permeance of the film samples was calculated from the mass loss rate, temperature, humidity, cup dimensions, and film thickness and are given in Table 1. The edge mask, still air resistance, and surface resistance corrections were applied to the raw values obtained. The water transmission rate was high enough that buoyancy correction is not necessary. Results clearly indicate that the film allows the passage of water vapor sufficient to aid in wound healing.

TABLE 1

Water Vapor Transmission results for poly(urea-urethane) film samples.

| Sample | Permeance (ng $s^{-1}$ $m^{-2}$ $mmHG^{-1}$) |
|---|---|
| 1 | 864 |
| 2 | 667 |
| 3 | 892 |
| 4 | 851 |

Example 11

A poly(urea-urethane) formulation sample prepared according to Example 1 was tested for systemic toxicity [acute, injection] in accordance with test method ANSI/AAMI/ISO 10993-11; 3-day gross observations of toxicity in mouse after single IP injection of 70° C./24 hr saline and vegetable oil extracts; five albino naïve mice per extract, five mice per control.

Acceptance Criteria: The test article meets the USP requirements if none of the animals treated with the test article extract show a significantly greater biological reactivity than those treated with the control.

Results: The test article met the requirements of the USP Systemic Injection test using the extracting media and conditions listed, as no significant biological reactivity was observed.

Example 12

A poly(urea-urethane) formulation sample prepared according to Example 1 was tested for delayed hypersensitivity [sensitization] in accordance with ANSI/AAMI/ISO 10993-10; The repeated patch method of Buehler was used to determine dermal sensitization reaction, but was modified to include a longer induction exposure period. Ten test guinea pigs were patched on shaved areas with the test article and five guinea pigs with the negative control. The test article was dosed neat and similar patches were prepared for the controls. Animals were wrapped with an elastic bandage secured with hypoallergenic tape. Bandages and patches were removed after at least six hr of exposure. At 24+/−2 hr [rest period] the sites were assessed for erythema and edema. The procedure was repeated at days 7 and 14 for at total of three inductions. Following a two-week rest period the animals were topically challenged with the appropriate test or control articles. The challenge patches were removed after at least six hr of exposure. The dermal patch sites were again observed for erythema and edema at 24 and 48 hr after patch removal.

Acceptance Criteria: Test results are based on incidence and severity of the sensitization reaction. Any skin reaction scores received by the test group that are greater than the scores received by the negative control group are considered to represent significant sensitization Results: No adverse reactions were observed over the duration of the study and according to test criteria, there was no sensitization potential [0% incidence and 0% severity] of the test article for the animals used in this study.

Example 13

A poly(urea-urethane) formulation sample prepared according to Example 1 was tested for intracutaneous [Intradermal] Reactivity [irritation] in accordance with ANSI/AAMI/ISO 10993-10: dermal irritation potential was determined by applying 0.5 ml of the neat test article or negative control [tap water] to the shaved skin of the dorsal area of three albino rabbits for at least four hr. Observations for skin irritation [erythema, edema, necrosis] were done at one, 24, 48, and 72 hr after unwrapping, using diluted alcohol to lightly swab the skin.

Acceptance Criteria: The requirements of the test are met if the difference between the test sample and the vehicle blank score is 1.0 or less for all animals Results: The requirements for the stated test were met. There was no significant dermal reaction observed at the test or control sites at any observation period for any animal [score=0].

Example 14

A poly(urea-urethane) formulation sample prepared according to Example 1 was tested for cytotoxicity using an ISO elution test [MEM extract] in accordance with USP 87 and ANSI/AAMI/ISO 10993-5; cell culture medium elution method on slightly subconfluent mouse L-929 cells. Three tests and one control were made with 37° C./24 hr extracts. Reactivity and cytotoxicity were determined after 48 hr of incubation of the extracts with the cells.

Acceptance Criteria: Conditions of cell cultures are interpreted according to a cytotoxicity scale according to criteria in ANSI/AAMI/ISO 10993-5. Samples are considered non-cytotoxic if the condition of the cell cultures indicates no cell lysis and discrete intracytoplasmic granules.

Results: The test article showed no to slight cytotoxicity according to the scoring criteria in ISO 10993 in this sensitive, direct-contact test.

Example 15

A poly(urea-urethane) formulation sample prepared according to Example 1 was tested for cytotoxicity using an Agar overlay test: This test evaluates the cytotoxicity of diffusible components from materials or solutions on mouse embryo fibroblast monolayers [L929 cells]. An agar layer is added over slightly subconfluent confluent cell monolayers to protect cells from mechanical damage. The sample is applied to sterile filter paper discs; four discs were placed directly on the agar layer and the cells were incubated for 24 hr.

Acceptance Criteria: The test sample meet USP requirements if none of the cell culture exposed to the sample shows greater than a mild reactivity [grade 2].

Results: Following incubation, the cells were evaluated microscopically using the grading evaluation criteria stated in the report. All results indicated a grade of "2" [borderline failure].

Example 16

A poly(urea-urethane) formulation sample prepared according to Example 1 was tested for genotoxicity using a Chromosome Aberration Test: Chinese Hamster Ovary cells were treated with saline and PEG extracts of the product film [37 C for 72 hr] in the presence and absence of S9 metabolic activation, which is used to screen for mutagens from byproducts of the sample. 'Activated' cells were exposed to test and control extracts for 3 to 4 hr; Non-activated cells were exposed to test and control extracts for 16 to 18 hr. Before harvest, cells were examined for cytotoxicity. Cells were then harvested, fixed, stained with Giemsa, coverslipped and examined microscopically for chromosome aberrations. All tests were in triplicate.

Acceptance Criteria: cytotoxicity is scored on a scale of 0 to 4 and number and types of various chromosome aberrations are scored for positive and negative controls and the test extracts, which must be within ranges showed by the negative controls to be considered non-genotoxic Results: There were no cytotoxic effects of the test extracts under any condition; polyploid, endoduplication rate and mitotic index in the treated samples were the same as the negative controls, indicating that the product is not genotoxic.

Example 17

A sample prepared according to Example 1 was tested mutagenicity with in vitro mouse lymphoma cells: Saline and polyethylene glycol extracts [37 C for 72 hr] were made of 72 $cm^2$ of the polymer films and were used to treat indicator cells per ISO 10993:3. Again the S9 activation system was used to screen for mutagens from byproducts of the test sample. Negative and positive controls are run concurrently with the test article to provide ranges of spontaneous and inducible mutant frequencies.

Acceptance Criteria: the assay must first be determined valid with negative and positive controls over the assay range before determination of mutant frequencies and cloning efficiency.

Results: saline and PEG controls performed as required, validating the assay with these extracts, which produced results well within the range of the negative controls, indicating that the product is not mutagenic. Saline and polyethylene glycol extracts were made of 72 $cm^2$ of the polymer films and were used to treat the indicator organism [Salmonella]. Again the S9 activation system was used to screen for mutagens from byproducts of the test sample Acceptance Criteria: for a mutagen, a two-fold increase in the number of revertants compared to the negative control Results: the extracts did not produce a two-fold increase in the number of revertants in any of the 5 test strains and spot tests showed no zone of reversion or of toxicity, indicating that the product is not mutagenic.

Example 18

A formulation according to Example 1 was applied to fire ant bites on a subjects hands and feet. Itching subsided almost immediately.

Example 19

A formulation according to Example 1 was applied to spider bites and immediately the itching and burning subsided. No additional harmful effects from the bite were observed.

Example 20

A formulation according to Example 1 was applied to the arms of a subject with extensive dermatitis from poison ivy. After an brief burning, the pain, itching and swelling subsided.

Example 21

A formulation according to Example 1 was applied to a deep 2" cut on the palm of a subjects hand. The wound was held closed for approximately 30 seconds by which time the formulation had dried and cured, holding the wound closed and stopping bleeding. The associated pain and throbbing subsided.

Example 22

A formulation according to Example 1 was applied to a severe abrasion on a subject's knee. After a very brief period of stinging, the pain subsided, the bleeding stopped and the resulting polymer film formed a protective bandage over the damaged skin.

Example 23

A formulation according to Example 1 was applied to a rash resulting from psoriasis. Itching and burning subsided and the resulting polymer film formed a protective film over the rash.

Example 24

A formulation according to Example 1 was applied to a herpes sore providing relief from itching and burning and providing a protective barrier over the blisters.

Example 25

A formulation according to Example 1 was applied to rash resulting from pityriasis rosea. The itching and redness subsided and the resulting polymer film formed a protective coating over the rash.

Example 26

A formulation according to Example 1 was applied to a sever sunburn of the scalp. Pain and discomfort subsided and the polymer film formed a protective coating over the burned skin.

Example 27

A formulation according to Example 1 was applied to a burn on a subjects hand. The pain and swelling subsided and the polymer film provided a protective coating over the damaged skin.

Example 28

A formulation according to Example 1 was applied to surgical stitches and formed a protective coating.

Having thus described certain embodiments of the present invention, it is to be understood that the invention defined by the appended claims is not to be limited by particular details set forth in the above description as many apparent variations thereof are possible without departing from the spirit or scope thereof as hereinafter claimed. The following claims are provided to ensure that the present application meets all statutory requirements as a priority application in all jurisdictions and shall not be construed as setting forth the full scope of the present invention.

We claim:

1. A method of treating a skin ailment comprising topically administering to a subject in need thereof a therapeutically effective amount of a composition comprising a poly(urea-urethane) polymer,
    wherein the skin ailment comprises at least one of the ailments selected from the group consisting of psoriasis, bites or stings, burns, sores, hemorrhoids, anal sphincter muscle tears, and cuts and scrapes, and
    wherein the poly(urea-urethane) polymer is prepared from a mixture comprising:
    (i) a primary polyamine;
    (ii) a secondary aromatic polyamine;
    (iii) a polyisocyanate; and
    (iv) optionally, a polyol.

2. The method of claim 1, wherein the primary polyamine comprises a polyether.

3. The method of claim 1, wherein the primary polyamine comprises polyoxypropylenediamine.

4. The method of claim 1, wherein the secondary aromatic polyamine comprises N,N-dialkylaminodiphenylmethane.

5. The method of claim 1, wherein the polyisocyanate comprises at least one of diphenymethanediisocyanate (MDI), a modified form of monomeric MDI, MDI containing resin, aliphatic diisocyanates, aromatic diisocyanates, alicyclic diisocyanates, ethylene diisocyanate, ethylidene diisocyanate, propylene diisocyanate, butylene diisocyanate, cyclopentylene-1,3-diisocyanate, cyclohexylene-1,4,diisocyanate, cyclohexylene-1,2-diisocyanate, 2,4-tolylene diisocyanate, 2,6-tolylene diisocyanate, 4,4'-diphenylmethane diisocyanate, 2,2-diphenylpropane-4,4'-diisocyanate, p-phenylene diisocyanate, m-phenylene diisocyanate, xylylene diisocyanate, 1,4-naphthylene diisocyanate, 1,5-naphthylene diisocyanate, diphenyl-4,4'-diisocyanate, azobenzene-4,4'diisocyanate, diphenylsulfone-4,4'diisocyanate, dichlorohexamethylene diisocyanate, tetramethylene diisocyanate, pentamethylene diisocyanate, hexamethylene diisocyanate, 1-chlorobenzene-2,4-diisocyanate, furfurylidene diisocyanate and triphenylmethane triisocyanate.

6. The method of claim 5, wherein the polyisocyanate comprises MDI, a modified form of monomeric MDI and/or a MDI containing resin.

7. The method of claim 1, wherein the polyisocyanate comprises a carbodiimide modified MDI.

8. The method of claim 1, wherein the polyol comprises at least one of ethylene glycol, propylene glycol, 1,3-butylene glycol, 1,4-butylene glycol, 2,3-butylene glycol, a propylene oxide adduct of trimethylol propane, polyethylene glycol 200, polyethylene glycol 400 and polyethylene glycol 600.

9. The method of claim 8, wherein the polyol comprises at least one of ethylene glycol, propylene glycol and a propylene oxide adduct of trimethylol propane.

10. The method of claim 1, wherein the composition further comprises a non-aqueous solvent selected from the group consisting of acetone, methyl ethyl ketone, methylisobutylketone, N-methylcyclohexanone, acetaldehyde, propionaldehyde, butyraldehyde, isobutyraldehyde, methyl acetate, ethyl acetate, butyl acetate, and methyl propyl acetate.

11. The method of claim 1, wherein the volume ratio of the primary polyamine in the composition ranges from about 3.6% to about 12.2% v/v, based on the total volume of the composition.

12. The method of claim 3, wherein the ratio of the primary polyamine and secondary aromatic polyamine to the polyisocyanate in the composition is from about 2.8:1 to about 3.8:1 by volume.

13. The method of claim 1, wherein the composition further comprises a colorant and/or pigment.

14. The method of claim 1, wherein the composition further comprises an antibacterial, antifungal and/or antiviral medicament.

15. The method of claim 1, wherein the poly(urea-urethane) polymer is prepared by reacting at least one of a primary polyamine, a secondary aromatic polyamine and a polyol with a polyisocyanate.

16. The method of claim 1, wherein the skin ailment is psoriasis.

17. The method of claim 1, wherein the skin ailment is bites or stings.

18. The method of claim 1, wherein the skin ailment is burns.

19. The method of claim 1, wherein the skin ailment is sores.

20. The method of claim 1, wherein the skin ailment is hemorrhoids.

21. The method of claim 1, wherein the skin ailment is anal sphincter muscle tears.

22. The method of claim 1, wherein the skin ailment is cuts and scrapes.

* * * * *